(12) United States Patent
Bell, III et al.

(10) Patent No.: US 8,828,681 B2
(45) Date of Patent: Sep. 9, 2014

(54) HOST CELLS WITH ARTIFICIAL ENDOSYMBIONTS

(71) Applicant: Bell Biosystems, Inc., Palo Alto, CA (US)

(72) Inventors: Caleb B. Bell, III, San Mateo, CA (US); Alexey Bazarov, Fremont, CA (US)

(73) Assignee: Bell Biosystems, Inc., Palo Alto, CA (US)

( * ) Notice: Subject to any disclaimer, the term of this patent is extended or adjusted under 35 U.S.C. 154(b) by 0 days.

(21) Appl. No.: 13/838,717

(22) Filed: Mar. 15, 2013

(65) Prior Publication Data

US 2013/0253303 A1     Sep. 26, 2013

Related U.S. Application Data

(63) Continuation-in-part of application No. 13/374,799, filed on Jan. 13, 2012.

(51) Int. Cl.
| | | |
|---|---|---|
| *C12Q 1/02* | (2006.01) | |
| *A61K 49/18* | (2006.01) | |
| *A61N 2/12* | (2006.01) | |
| *A61B 5/05* | (2006.01) | |
| *B82Y 5/00* | (2011.01) | |
| *B82Y 15/00* | (2011.01) | |

(52) U.S. Cl.
CPC .............. *A61B 5/05* (2013.01); *A61K 49/1896* (2013.01); *B82Y 5/00* (2013.01); *A61N 2/12* (2013.01); *B82Y 15/00* (2013.01)
USPC ......... 435/29; 435/252.1; 435/455; 424/9.34; 424/93.4

(58) Field of Classification Search
None
See application file for complete search history.

(56) References Cited

U.S. PATENT DOCUMENTS

| | | | |
|---|---|---|---|
| 4,385,119 A | 5/1983 | Blakemore | |
| 4,677,067 A | 6/1987 | Schwartz et al. | |
| 6,004,815 A | 12/1999 | Portnoy et al. | |
| 6,287,556 B1 | 9/2001 | Portnoy et al. | |
| 6,599,502 B2 | 7/2003 | Portnoy et al. | |
| 7,390,646 B2 | 6/2008 | Andino-Pavlovsky et al. | |
| 7,470,427 B2 | 12/2008 | Cocking | |
| 7,754,221 B2 | 7/2010 | Szalay et al. | |
| 8,159,224 B2 | 4/2012 | Fontius | |
| 2002/0012698 A1 | 1/2002 | Bauerlein et al. | |
| 2004/0234455 A1 | 11/2004 | Szalay | |
| 2005/0069491 A1 | 3/2005 | Szalay et al. | |
| 2007/0202572 A1 | 8/2007 | Szalay et al. | |
| 2007/0258886 A1 | 11/2007 | Ahrens et al. | |
| 2007/0275924 A1 | 11/2007 | Khan | |
| 2009/0181101 A1* | 7/2009 | Rademacher et al. | 424/499 |
| 2009/0325258 A1 | 12/2009 | Matsunaga et al. | |
| 2010/0135912 A1* | 6/2010 | Gambhir et al. | 424/9.32 |
| 2010/0297022 A1 | 11/2010 | Prato et al. | |
| 2011/0034753 A1 | 2/2011 | Dobson et al. | |
| 2012/0021517 A1 | 1/2012 | Jin et al. | |
| 2012/0184004 A1 | 7/2012 | Kay et al. | |
| 2012/0184030 A1 | 7/2012 | Dermanovic et al. | |
| 2012/0302819 A1 | 11/2012 | Alphandery | |
| 2013/0224122 A1 | 8/2013 | Gambhir et al. | |

FOREIGN PATENT DOCUMENTS

EP     1807517 B1     10/2011

OTHER PUBLICATIONS

U.S. Appl. No. 90/008,857, filed Oct. 7, 2008, Portnoy, Daniel A. et al.
U.S. Appl. No. 90/008,859, Sep. 30, 2008, Portnoy, Daniel A. et al.
U.S. Appl. No. 90/008,860, Oct. 14, 2008, Portnoy, Daniel A. et al.
Agapakis, C.M. et al., Towards a synthetic chloroplast, PLoS ONE, Apr. 6, 2011: e18877.
Ben-Haim, N. et al., Cell-specific integration of artificial organelles based on functionalized polymer vesicles, Nano Lett., 2008, 8:1368-1373.
Benoit, M.R. et al., Visualizing implanted tumors in mice with magnetic resonance imaging using magnetotactic bacteria, Clin. Canc. Res., Aug. 15, 2009, 15(16):5170-5177.
Benoit, M.R. et al., Supp. Figs., Clin. Canc. Res. 2009, at: http://clincancerres.aacrjournals.org/content/suppl/2009/08/11/1078-0432.CCR-08-3206.DC1/Supplementary_Dala.pdf.
Bernsen, M.R. et al., Labelling of mammalian cells for visualisation by MRI, Eur. Radiol., 2010, 20: 255-274.
Bhattacharya, D. et al., Photosynthetic eukaryotes unite: endosymbiosis connects the dots, BioEssays, 2003, 26:50-60.
Bielecki, J. et al., *Bacillus subtilis* expressing a haemolysin gene from Listeria monocytogenes can grow in mammalian cells, Nature, May 10, 1990, 345:175-176.
Bitterman, P.B. et al., Alveolar macrophage replication, J. Clin. Inv., Aug. 1984, 74: 460-469.
Blakemore, R., Magnetotactic bacteria, Science, Oct. 24, 1975, 190(4212): 377-379.
Blakemore, R.P. et al., Isolation and pure culture of a freshwater magnetic spirillum in chemically defined medium, J. Bacteriol. Nov. 1979, 140(2): 720-729.
Bonnett, H.T., On the mechanism of the uptake of Vaucheria chloroplasts by carrot protoplasts treated with polyethylene glycol, Planta, 1976, 131: 229-233.
Brown, M.B. et al., Exploiting tumour hypoxia in cancer treatment, Nat. Rev. Cancer, Jun. 2004, 4: 437-447.
Budde, M.B. et al., Magnetic tagging of therapeutic cells for MRI, J. Nucl. Med., Feb. 2009, 50(2): 171-174.

(Continued)

*Primary Examiner* — Jim Ketter
(74) *Attorney, Agent, or Firm* — HelixIP LLP

(57) ABSTRACT

The present invention is directed generally to eukaryotic cells comprising single-celled organisms that are introduced into the eukaryotic cell through human intervention and which transfer to daughter cells of the eukaryotic cell through at least five cell divisions, and methods of introducing such single-celled organisms into eukaryotic cells. The invention also provides methods of using such eukaryotic cells. The invention further provides single-celled organisms that introduce a phenotype to eukaryotic cells that is maintained in daughter cells. The invention additionally provides eukaryotic cells containing magnetotactic bacteria.

32 Claims, 3 Drawing Sheets

(56) References Cited

OTHER PUBLICATIONS

Bulte, J.W.M., In vivo MRI cell tracking: clinical studies, AJR Am. J. Roentgenol., Aug. 2009, 193(2): 314-325.

Burdette, D.L. et al., Vibrio VopQ induces PI3-kinase-independent autophagy and antagonizes phagocytosis, Mol. Microbiol., 2009, 73(4): 639-649.

Burgess, J.G. et al., Evolutionary relationships among Magnetospirillum strains inferred from phylogenetic analysis of 16S rDNA sequences, J. Bacteriol., 1993, 175: 6689-6694.

Camilli, A. et al., Listeria monocytogenes mutants lacking phosphatidylinositol-specific phospholipase C are avirulent, J. Exp. Med., Mar. 1991, 173: 751-754.

Cao, F. et al., In vivo visualization of embryonic stem cell survival, proliferation, and migration after cardiac delivery, Circulation, 2006, 113:1005-1014.

Cheng, K. et al., Magnetic enhancement of cell retention, engraftment, and functional benefit . . . , Cell Transplant., 2012, 21: 1121-1135.

Chico-Calero, I. et al., Hpt, a bacterial homolog of the microsomal glucose-6-phosphate translocase . . . , Proc. Natl Acad. Sci., Jan. 8, 2002, 99(1): 431-436.

Chomel, B.B. et al., Ecological fitness and strategies of adaptation of *Bartonella* species to their hosts and vectors, Vet. Res., 2009, 40: 29.

Cocking, E.C., et al., Symbiosome-like intracellular colonization of cereals and other crop plants by nitrogen-fixing bacteria . . . , Chin. Acad. Sci., 2005, 48: 888-896.

Cocking, E.C., et al., Intracellular colonization of roots of *Arabidopsis* and crop plants by *Gluconacetobacter diazotrophicus*, In Vitro. Cell. Dev. Biol., 2006, 42: 74-82.

Concord, C. et al., Long-term evolutionary stability of bacterial endosymbiosis in Curculionoidea . . . , Mol. Biol. Evol., 2008, 25(5): 859-868.

Corchero, J.L. et al., Biomedical applications of distally controlled magnetic nanoparticles, Trends Biotechnol., 2009, 27(8): 468-476.

Dale, C. et al., The insect endosymbiont *Sodalis glossinidius* utilizes a type III secretion system for cell invastion, Proc. Natl Acad. Sci., Feb. 13, 2001, 98(4): 1883-1888.

Dang, L.H., et al., Combination bacteriolytic therapy for the treatment of experiemental tumors, Proc. Natl Acad. Sci., Dec. 18, 2001, 98(26): 15155-15160.

Dubreuil, R. et al., Bringing host-cell takeover by pathogenic bacteria to center stage, Cell. Logist., 2011, 1(4): 120-124.

Dyall, S.D. et al., Ancient invasions: from endosymbionts to organelles, Science, 2004, 304: 253-257.

Faivre, D. et al., Magnetotactic bacteria and magnetosomes, Chem. Rev. 2008, 108: 4875-4898.

Felfoul, O. et al., MR imaging of Fe-Co nanoparticles, magnetolactic bacteria . . . , Proc. of the 7th IEEE International. Conf. on Nanotech., 2008, pp. 308-311.

Finlay, B.B. et al., Common themes in microbial pathogenicity revisited, Microbiol. Mol. Biol. Rev., Jun. 1997, 61(2): 136-169.

Fritsche, T.R. et al., Phylogenetic diversity among geographically dispersed *Chlamydiales endosymbionts*. . . , Appl. Environ. Microbiol., Jun. 2000, 66(6): 2613-2619.

Goebel, W. et al., Intracellular survival strategies of mutualistic and parasitic prokaryotes, Trends Microbiol., Jun. 2001, 9(6): 267-273.

Goetz, M. et al., Microinjection and growth of bacteria in the cytosol of mammalian host cells, Proc. Natl Acad. Sci., Oct. 9, 2001, 98(21): 12221-12226.

Gordon, S. et al., Monocyte and macrophage heterogeneity, Nat. Rev., Dec. 2005, 5: 953-964.

Gupta, R.S. et al., Phylogenomics and signature proteins for the alpha *Proteobacteria* and its main groups, BMC Microbiol., Nov. 28, 2007, 7:106.

Hackam, D.J. et al. Rho is required for the initiation of Calcium signaling and phagocytosis by Fcγ receptors in macrophages, J. Exp. Med., Sep. 15, 1997, 186(6): 955-966.

Hacker, H. et al., Caspase-9/-3 activation and apoptosis are induced in mouse macrophage upon ingestion and digestion of *E. coli* bacteria, J. Immunol., 2002, 169: 3172-3179.

Hayward, R.D. et al., Direct nucleation and bundling of actin by the SipC protein of invasive *Salmonella*, EMBO J., 1999, 18(18): 4926-4934.

Himmerlreich, U. et al., Stem cell labeling for magnetic resonance imaging, Min. Inv. Ther., 2008, 17:132-142.

Hong, P.C. et al., Identification of genes required for chronic persistence of *Brucella abortus* in mice, Infect. Immun., Jul. 2000, 68(7): 4102-4107.

Huang, J. et al., Phylogenomic evidence supports past endosymbiosis, intracellular and horizontal gene transfer in *Cryptosporidium parvum*, Genome Biol., Oct. 19, 2004, 5:R88.

Joseph, B. et al., Identification of Listeria monocytogenes contributing to intracellular replication by expression profiling . . . , J. Bacteriol., Jan. 2006, 188(2): 556-568.

Judas, M. et al., Genomic islands tools of bacterial horizontal gene transfer and evolution, FEMS Microbiol. Rev., 2009, 33: 376-393.

Jutila, M.A. et al., Locally dividing macrophages in normal and inflamed mammary glands, Clin. Exp. Immunol., 1986, 66: 615-624.

Kasinaskas, R.W. et al., *Salmonella typhimurium* lacking ribose chemoreceptors localize in tumor quience and induce apoptosis, Cancer Res., 2007, 67(7): 3201-3209.

Kawaguchi, R. et al., Phylogeny and 16s rRNA sequence of *Magnetospirillum* sp. AMB-1, an aerobic magnetic bacterium, Nucleic Acids, Res., 1992, 20(5): 1140.

Kimura, N.T. et al., Selective localization and growth of *Bifidobacterium bifidum* in mouse tumors following intravenous administration, Cancer Res., Jun. 1980, 40: 2061-2068.

Kircher, M.F. et al., Noninvasive cell-tracking methods, Nat. Rev. Clin. Oncol., 2011, 8:677-688.

Kraitchman, D.L. et al., Imaging of stem cells using MRI, Basic Res. Cardiol., 2008, 103: 105-113.

Kraitchman, D.L. et al., Stem cell therapy: MRI guidance and monitoring, 2008, J. Magn. Reson. Imaging 27: 299-310.

Lane, C.E. et al., The eukaryotic tree of life: endosymbiosis takes its TOL, Trends Ecol. Evol., 2008, 23(5): 268-275.

Lang, C. et al., Expression of green fluorescent protein fused to magnetosome proteins in microaerophilic magnetotactic bacteria, Appl. Environ. Microbial., 2008, 74: 4944-53.

Lee, Z. et al., Imaging stem cell implant for cellular-based therapies, Exp. Biol. Med., 2008, 233: 930-940.

Lemmon, M.J. et al., Anaerobic bacteria as a gene delivery system that is controlled by the tumor microenvironment, Gene Ther., 1997, 4: 791-796.

Li, L.H. et al., Electrofusion between heterogeneous-sized mammalian cells in a pellet: potential applications in drug delivery . . . , Biophysical J., Jul. 1996, 71: 479-486.

Liu, S. et al., Anticancer efficacy of systemically delivered anaerobic bacteria as gene therapy vectors targeting tumor hypoxia/necrosis, Gene Ther., 2002, 9: 291-296.

Loessner, H. et al., Remote control of tumour-targeted *Salmonella entrerica serovar Typhimurium* by the use of L-arabinose . . . , Cell. Microbiol., 2007, 9(6): 1529-1537.

Login, F.H. et al., Antimicrobial peptides keep insect endosymbionts under control, Science, Oct. 21, 2011, 334: 362-365.

Long, C.M. et al., In vivo tracking of cellular therapeutics using magnetic resonance imaging, Expert Opin. Biol. Ther., 2009, 9(3): 293-306.

Long, M.E. et al., Disruption of *Francisella tularensis* schu S4 iglI, iglJ, and pdpC genes results in attenuation . . . , Infect. Immun., Mar. 2013, 81(3): 850-861.

Martel, S. et al., Towards MRI-controlled ferromagnetic and MC-1 magnetotactic bacterial carriers . . . , Proceed. 28th IEEE EMBS Ann. Intl Conf. NY, 2006, pp. 3399-3402.

Matsunaga, T. et al., Phagocytosis of bacterial magnetite by leucocytes, Appl. Microbiol. Biotechnol., 1989, 31:401-405.

Matsunaga, T. et al., Gene transfer in magnetic bacteria: transposon mutagenesis and cloning of genomic DNA fragments . . . , J. Bacteriol., May 1992, pp. 2748-2753.

Matsunaga, T. et al., Complete genome sequence of the facultative anaerobic magnetotactic bacterium *Magnetospirillum* sp. strain AMB-1, DNA Res., 2005, 12: 157-166.

(56) References Cited

OTHER PUBLICATIONS

Matsunaga, T. et al., Molecular bioengineering of bacterial magnetic particles . . . , Magnetoreception and Magnetosomes in Bacteria, 2006, pp. 227-254, Springer-Verlag, Berlin.
Min, J. et al., Quantitative bioluminescence imaging of tumor-targeting bacteria in living animals, Nat. Protocols, 2008, 3(4): 629-636.
Nishida, K. et al., Induction of biogenic magnetization and redox control by a component of the target of rapamycin complex 1 signaling pathway, PLoS Biol., 2012, 10:e1001269.
Okamoto, N. et al., A secondary symbiosis in progress?, Science, Oct. 14, 2005, 310: 287.
Oldroyd. G.E.D. et al., Reprogramming plant cells for endosymbiosis, Science, May 8, 2009, 324: 753-754.
O'Riordan, M. et al., Innate recognition of bacteria by a macrophage cytosolic surveillance pathway, Proc. Natl Acad. Sci., Oct. 15, 2002, 99(21): 13861-13866.
Pan, X. et al., Cationic lipid-coated magnetic nanoparticles associated with transferrin for gene delivery, Int. J. Pharm., Jun. 24, 2008, 358: 263-70.
Pawelek, J.M. et al., Tumor-targeted *Salmonella* as a novel anticancer vector, Cancer Res., Oct. 15, 1997, 57: 4537-4544.
Price, C.T.D. et al., Amoeba host-Legionella synchronization of amino acid auxotrophy and its role in bacterial adaptation . . . , Environ. Microbiol., 2013, 16(2): 350-358.
Qiu, B. et al., Dual transfer of GFP gene and MGd into stem-progenitor cells, Acad. Radiol., 2010, 17: 547-552.
Riegler, J. et al., Superparamagnetic iron oxide nanoparticle targeting of MSCs in vascular injury, Biomaterials, 2013, 34: 1987-1994.
Rogers, W.J. et al., Technology insight: in vivo cell tracking by use of MRI, Nature Clin. Prac., Oct. 2006, 3(10): 554-562.
Roodbeen R. et al., Synthetic cells and organelles: compartmentalization strategies, BioEssays, 2009, 31: 1299-1308.
Salminen, M. et al., Improvement in nuclear entry and transgene expression of baculoviruses by disintegration of microtubules . . . , J. Virol., Mar. 2005, 79(5): 2720-2728.
Schaffer, D. et al., Biological imaging in animals with genetically encoded magnetic reporters, Jan. 30, 2013, at http://www.berkeley.edu/news2/2013/01/KeckAbstract.htm.
Scheffel, A. et al., The acidic repetitive domain of the *Magnetospirillum gryphiswaldense* MamJ protein . . . , J. Bacteriol., Sep. 2007, 189(17): 6437-6446.
Schoen, P. et al., Gene transfer mediated by fusion protein hemagglutinin reconstituted in cationic lipid vesicles, Gene Ther., 1999, 6:823-832.
Schuler, D. et al., Dynamics of iron uptake and Fe3O4 biomineralization during aerobic and microaerobic growth . . . , J. Bacteriol., 1998, 180(1): 159-162.
Schuler, D. et al., Bacterial magnetosomes: microbiology, biomineralization, and biotechnological applications, Appl. Microbiol. Biotechnol., 1999, 52: 464-473.
Schultheiss, D. et al., Inactivation of the flagellin gene flaA in *Magnetospirillum gryphiswaldense* . . . , Appl. Environ. Microbiol., Jun. 2004, 70(6): 3624-2631.
Shoemaker, R.H., The NCI60 human tumour cell line anticancer drug screen, Nature Rev., Oct. 2006, 6: 813-823.
Silva, A.C. et al., Application of hyperthermia induced by superparamagnetic iron oxide nanoparticles in glioma treatment, Intl J. Nanomed., 2011, 6:591-603.
Smith, G.A. et al., The two distinct phospholipases C of *Listeria monocytogenes* have overlapping roles . . . , Infect. Immun., Nov. 1995, 63(11): 4231-4237.
Soghomonyan, S.A. et al., Positronic emissions tomography (PET) imaging of tumor-localized *Salmonella* expressing HSV1-TK, Cancer Gene Ther., 2005, 12: 101-108.
Stewart, F.J. et al., Lateral symbionts acquisition in a maternally transmitted chemosynthetic clam endosymbiosis, Mol. Biol. Evol., 2008, 25(4): 673-687.
Sugimoto, Y. et al., Differential cell division history between neutrophils and macrophages, British J. of Haematology, 2006, 135: 725-731.
Swiston, A.J. et al., Surface functionalization of living cells with multilayer patches, Nano Lett., 2008, 8(12): 4446-4453.
Sznol, M. et al., Use of preferentially replicating bacteria for the treatment of cancer, J. Clin. Invest., Apr. 2000, 105(8): 1027-1030.
Thao, M.L. et al., Phylogenetic analysis of vertically transmitted psyllid endosymbionts (*Candidatus Carsonella ruddi*) . . . , Curr. Microbiol., 2001, 42: 419-421.
Vaishnava, S. et al., The cell biology of secondary endosymbiosis—how parasites build, divide and segregate the apicoplast, Mol. Microbiol., 2006, 61(6): 1380-1387.
Valdivia R.H. et al., Endosymbiosis: the evil within, Current Biology, 2007, 17 (11): R408-R410.
Van Der Glezen, M., Endosymbiosis: past and present, Heredity, 2005, 95: 335-336.
Van Furth, R. et al., Dual origin of mouse spleen macrophages, J. Exp. Med., Nov. 1984, 160: 1273-1283.
Verhoeven, H.A. et al., Direct cell to cell transfer of organelles by microinjection, Plant Cell Reports, 1992, 10: 613-616.
Wajnberg, E. et al., Electron paramagnetic resonance study of the migratory ant *Pachycondyla marginata* abdomens, Biophys. J., Feb. 2000, 78: 1018-1023.
Wenergreen, J.J., Endosymbiosis: lessons in conflict resolution, PLoS Biology, Mar. 2004, 2(3): 307-311.
Widermann, A. et al., *Yersinia enterocolitica* invasin triggers phagocytosis via B1 integrins, CDC42Hs and WASp in macrophages, Cellular Microbiol., 2001, 3(10): 693-702.
Williams, K. et al., Proliferating cellular nuclear antigen expression as a marker of perivascular macrophages . . . , Am. J. Pathol., Aug. 2002, 161(2): 575-585.
Wyss Institute, New "magnetic yeast" could be significant step in harnessing nature's magnetic capabilities, Feb. 28, 2012, at http://wyss.harvard.edu/viewpressrelease/78.
Xi, Z. et al., Characterization of Wolbachia transfection efficiency by using microinjection of embryonic cytoplasm . . . , Appl. Environ. Microbiol., 2005, 71(6): 3199-3204.
Xie, J. et al., Production, modification, and bio-applications of magnetic nanoparticles gestated by Magnetotactic Bacteria, Nano Res., 2009, 2: 261-278.
Yam, C. et al., Monotherapy with a tumor-targeting mutant of *S. typhimurium* inhibits liver metastasis in a mouse model . . . , J. Surgical Res., 2010, 164: 248-255.
Yoshida, S. at al., Shigella deliver an effector protein to trigger host microtubule destabilization . . . , EMBO J., 2002, 21(12): 2923-2936.
Zhang, X. at al., Artificial innate immune system . . . , Proc. of the 3rd Int'l Conf. on Artificial Immun. Sys. (ICARIS), LNCS 3239, 2004, pp. 302-315.
Zhao, M. et al., Targeted therapy with a *Salmonella typhimurium* leucine-arginine auxotroph . . . , Cancer Res., Aug. 1, 2006, 66(15): 7647-7652.
Zhao, M., et al., Monotherapy with a tumor-targeting mutant of *Salmonella typhimurium* . . . , Proc. Natl. Acad. Sci., Jun. 12, 2007, 104(24): 10170-10174.

\* cited by examiner

Panel B

Panel A

HOST CELLS WITH ARTIFICIAL ENDOSYMBIONTS

CROSS-REFERENCES TO RELATED APPLICATION(S)

This application is a continuation-in-part of U.S. application Ser. No. 13/74,799, filed on Jan. 13, 2012, and is a continuation-in-part of International Application No. PCT/US2013/021414, filed on Jan. 14, 2013, which is a continuation-in-part of U.S. application Ser. No. 13/374,799, the entire contents of which applications are hereby incorporated by reference in its entirety for all purposes.

FIELD OF THE INVENTION

The present invention relates generally to the field of endosymbiosis, artificial endosymbionts, and magnetotactic bacteria. In particular, the invention provides single-cell organisms such as artificial endosymbionts including magnetotactic bacteria, eukaryotic cells to host those single-celled organisms, methods of using eukaryotic cells containing single-celled organisms, and methods of introducing the single-celled organisms into the eukaryotic cells.

BACKGROUND OF THE INVENTION

Mitochondria, chloroplast and other membrane bound organelles add heritable functionalities, such as photosynthesis, to eukaryotic cells. Such organelles (identified by their vestigial circular DNA) are believed to be endosymbiotically derived.

Bacteria exist with a wide range of functionalities not present in various eukaryotic cells. For example, in 1975 Blakemore identified magnetotactic bacteria (MTB) that orient and swim along a geomagnetic field. (Blakemore, R. Magnetotactic bacteria. *Science* 24: 377-379 (1975) (which is incorporated by reference in its entirety for all purposes)). These magnetotactic bacteria produce magnetic structures called magnetosomes that are composed of magnetite ($Fe_3O_4$) or greigite ($Fe_3S_4$) enclosed by a lipid membrane. (Id). A large number of MTB species have been identified since their initial discovery. (Id).

Magnetotactic bacteria have been used to selectively bind to and separate substances. (U.S. Pat. No. 4,677,067 (which is incorporated by reference in its entirety for all purposes)). Additionally, attempts have been made to add magnetic functionality to cells through external tags. (Swiston, A. J., Cheng, C., Soong, H. U., Irvine, D. J., Cohen, R. J., Rubner, M. F. Surface Functionalization of Living Cells with Multilayer Patches. *Nano Lett.* 8(12): 4446-53 (2008) (which is incorporated by reference in its entirety for all purposes)). Bacterial magnetite has also been introduced into red blood cells by cell fusion (Matsunaga, T., Kamiya, S., (1988), In: Atsumi, K., Kotani, M., Ueno, S., Katila T., Williamsen, S. J. (eds) 6th International Conference on Biomagnetisms (1987). Tokyo Denki University Press, Tokyo, pp. 50-51 (which is incorporated by reference in its entirety for all purposes)), and MTB have been introduced into granulocytes and monocytes by phagocytosis. (Matsunaga, T., Hashimoto, K., Nakamura, N., Nakamura, K., Hashimoto, S. Phagocytosis of bacterial magnetite by leucocytes. *Applied Microbiology and Biotechnology* 31(4): 401-405 (1989) (which is incorporated by reference in its entirety for all purposes)). However, none of these alterations are heritable to daughter cells.

It is an object of the present invention to provide eukaryotic cells containing a single-celled organism that is introduced into the eukaryotic cell through human intervention which transfers to daughter cells of the eukaryotic cell through at least five cell divisions, and which maintains sufficient copy number in the daughter cells so that a desired functionality introduced by the single-celled organism is maintained in the daughter cells. It is further an object of the present invention to provide eukaryotic host cells containing artificial endosymbionts that are heritable to daughter cells and methods of uses these eukaryotic cells. It is also an object of the present invention to provide methods of introducing artificial endosymbionts into the cytosol of eukaryotic host cells. It is another object of the present invention to provide eukaryotic cells with a heritable magnetic phenotype. It is also an object of the invention to provide methods of tracking, localizing, or damaging eukaryotic cells.

SUMMARY OF THE INVENTION

The present invention relates to eukaryotic cells comprising single-celled organisms, such as artificial endosymbionts, methods of using such eukaryotic cells, and methods of introducing such single-celled organisms into eukaryotic cells. In one embodiment, the single-celled organism provides the eukaryotic cell with a desired functionality. In one embodiment, the single-celled organisms are artificial endosymbionts heritable to daughter cells. In another embodiment, the artificial endosymbiont is a magnetotactic bacterium. In one embodiment, the magnetotactic bacterium provides the eukaryotic cell with a magnetic functionality. In one embodiment, a method of use is a method of detecting the eukaryotic cells. In another embodiment, a method of use is a method of magnetically manipulating or targeting the eukaryotic cells. In another embodiment, a method of use is a method of damaging the eukaryotic cells.

The artificial endosymbiont of the invention may be modified by deleting, adding, and/or mutating at least one gene whereby the artificial endosymbiont acquires a trait useful for endosymbiosis or biotrophy. The genes to be mutated, added, and/or deleted in the artificial endosymbiont may be genes encoding components of the flagellar assembly and genes encoding enzymes for synthesizing essential macromolecules, such as amino acids, nucleotides, vitamins, and co-factors. In certain embodiments, the MTB may further be modified to express an antibiotic resistance gene or other selectable marker.

In some embodiments the eukaryotic cells of the invention are mammalian, such as mouse, rat, rabbit, hamster, human, porcine, bovine, or canine. In another embodiment the artificial endosymbiont is transmitted from the host cell to daughter progeny host cells. In another embodiment, the method further comprises deleting, inserting, and/or mutating at least one gene from the eukaryotic cell.

The single-celled organisms of the invention can be introduced into eukaryotic cells by a number of methods known to those of skill in the art including, but not limited to, microinjection, natural phagocytosis, induced phagocytosis, macropinocytosis, other cellular internalization processes, liposome fusion, erythrocyte ghost fusion, or electroporation.

DETAILED DESCRIPTION OF THE INVENTION

Figure 1:
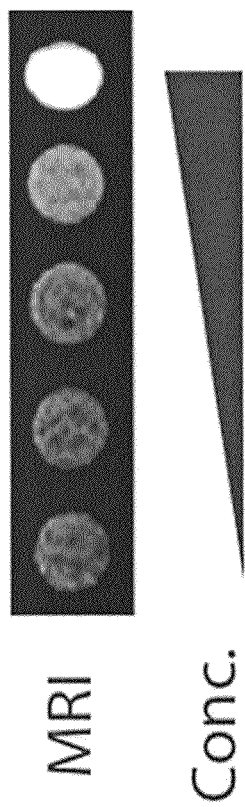
FIG. 1 shows positive contrast generated with a $T_1$ pulse sequence over a log scale concentration up to ~$10^8$ MTB/mL for gfp$^+$AMB suspended in agar plugs using a 1.5 T instrument to optimize and characterize the imaging properties.

The invention is illustrated by way of example and not by way of limitation. It should be noted that references to "an" or "one" or "some" embodiment(s) in this disclosure are not necessarily to the same embodiment, and all such references mean at least one.

The present invention is directed to eukaryotic cells containing single-celled organisms, such as host cells containing artificial endosymbionts in the cytosol of the host cell, and methods of introducing the single-celled organism into the eukaryotic cell. In one embodiment the single-celled organism is an artificial endosymbiont that is genetically altered. In some embodiments the single-celled organisms are magnetotactic bacteria (MTB).

Definitions

As used herein, the term "AMB" refers to *Magnetospirillum magneticum* strain AMB-1.

As used herein, the term "artificial endosymbiont" refers to a single-celled organism that is or has been introduced into the cytosol of a eukaryotic cell through human intervention, which has been or can be transferred to daughter cells of the eukaryotic cell through at least five cell divisions, and which maintains sufficient copy number in the daughter cells so that a phenotype introduced by the artificial endosymbiont is maintained in the daughter cells.

As used herein, the term "cellular life cycle" refers to series of events involving the growth, replication, and division of a eukaryotic cell. It is divided into five stages, known as $G_0$, in which the cell is quiescent, $G_1$ and $G_2$, in which the cell increases in size, S, in which the cell duplicates its DNA, and M, in which the cell undergoes mitosis and divides.

As used herein, the term "cytosol" refers to the portion of the cytoplasm not within membrane-bound sub-structures of the cell.

As used herein, the term "daughter cell" refers to cells that are formed by the division of a cell.

As used herein, the term "essential molecule" refers to a molecule needed by a host cell for growth or survival.

As used herein, the term "genetically modified" refers to altering the DNA of a cell so that a desired property or characteristic of the cell is changed.

As used herein, the term "host cell" refers to a eukaryotic cell in which an artificial endosymbiont can reside.

As used herein, the term "liposome mediated" refers to artificial microscopic vesicles consisting of an aqueous core enclosed in one or more lipid layers, used to convey artificial endosymbionts to host cells.

As used herein, the term "magnetosome" refers to particles of magnetite (i.e., $Fe_3O_4$) or greigite ($Fe_3S_4$) enclosed by a sheath or membrane, either as individual particles or in chains of particles.

As used herein, the term "magnetotactic bacteria" or "MTB" refers to bacteria with genes encoding magnetosomes.

As used herein, the term "mammal" refers to warm-blooded vertebrate animals all of which possess hair and suckle their young.

As used herein, the term "microinjection" refers to the injection of artificial endosymbionts into host cells.

As used herein, the term "tagged artificial endosymbiont" refers to artificial endosymbionts that have a ligand on the surface of the endosymbiont.

As used herein, the term "parent cell" refers to a cell that divides to form two or more daughter cells.

As used herein, the term "receptor mediated" refers to a molecular structure or site on the surface of a host cell that binds with an artificial endosymbiont or a tagged artificial endosymbiont followed by internalization of the artificial endosymbiont.

Artificial Endosymbionts

Single-celled organisms of the invention include bacteria that are capable of surviving in a eukaryotic cell and maintain copy number such that the phenotype introduced by the single-celled organism is maintained in daughter cells. In some embodiments, the single-celled organism does not kill the eukaryotic host cell without further human intervention. In some embodiments, the single-cell organism has a functionality that is acquired by the eukaryotic cell following the introduction of the single-celled organism. In some embodiments, the functionality of the single-cell organism is magnetism, production of a nutrient, desalinization, photosynthesis, or tolerance to harsh environmental challenges. Magnetism includes diamagnetism and paramagnetism. In some embodiments, the eukaryotic cell maintains the functionality for at least 48 hours. In some embodiments, the single-celled organism can stably maintain phenotype in the eukaryotic daughter cells through at least 3 cell divisions, or at least 4 division, or at least 5 divisions, or at least 6, 7, 8, 9, 10, 11, 12, 13, 14, 15, 16, 17, 18, 19, or 20 cell divisions. In another embodiment, the single-celled organism can stably maintain phenotype in the eukaryotic daughter cells through 3-5 divisions, or 5-10 divisions, or 10-15 divisions, or 15-20 divisions.

In an embodiment of the invention, the single-celled organisms of the invention are genetically modified. Methods for genetically modifying bacteria are well known in the art. Typically, the bacteria will be genetically modified to improve their survival in eukaryotic host cells, and/or to reduce the toxicity of the single-celled organism to the eukaryotic cell, and/or to provide the eukaryotic cell with a useful phenotype. In one embodiment, the flagellar proteins of a single-celled organism are modified so that the single-celled organism no longer expresses flagellar proteins in the eukaryotic host cell. In another embodiment, the single-celled organism is modified so that it can no longer synthesize an essential molecule that is preferably provided by the eukaryotic host cell. In an embodiment, the single-celled organism is genetically modified so that its cell cycle is coordinated with the cell cycle of the eukaryotic host cell so that copy number of the single-celled organism can be maintained at a sufficient level to impart the phenotype to daughter cells.

Embodiments of the invention include singled-celled organisms that are Proteobacteria. Embodiments of the invention include single-celled organisms that are α-Proteobacteria. In the current taxonomic scheme based on 16S rRNA, α-proteobacteria are recognized as a Class within the phylum Proteobacteria, and are subdivided into 7 main subgroups or orders (Caulobacterales, Rhizobiales, Rhodobacterales, Rhodospirillales, Rickettsiales, Sphingomonadales and Parvularculales). (Gupta, R. S. Phylogenomics and signature proteins for the alpha Proteobacteria and its main groups. *BMC Microbiology*, 7:106 (2007) (which is incorporated by reference in its entirety for all purposes)).

A large number of α-proteobacterial genomes that cover all of the main groups within α-proteobacteria have been sequenced, providing information that can be used to identify unique sets of genes or proteins that are distinctive characteristics of various higher taxonomic groups (e.g. families, orders, etc.) within α-proteobacteria. (Id. (which is incorporated by reference in its entirety for all purposes)).

Embodiments of the invention include single-celled organisms that are magnetotactic bacteria ("MTB"). A large number of MTB species are known to those of ordinary skill in the art since their initial discovery in 1975 by Blakemore (Blakemore, R. Magnetotactic bacteria. *Science* 24: 377-379 (1975) (which is incorporated by reference in its entirety for all purposes)) and represent a group of microbes (Faivre, D. & Schüller, D. Magnetotactic bacteria and magnetosomes. *Chemistry Reviews* 108: 4875-4898 (2008) (which is incorporated by reference in its entirety for all purposes)). MTB have been identified in different subgroups of the Proteobacteria and the *Nitrospira* phylum with most of the phylotypes grouping in α-Proteobacteria. Currently, culturable MTB strains assigned as α-Proteobacteria by 16S rRNA sequence similarity include the strain originally isolated by Blakemore in 1975, *Magnetospirillum magnetotactium* (formerly *Aquasprillium magnetotactium*), *M. gryphiswaldense, M. magneticum* strain AMB-1 ("AMB"), *M. polymorphum, Magnetosprillum* sp. MSM-4 and MSM-6, *Magnetococcus marinus*, marine vibrio strains MV-1 and MV-2, a marine spirillum strain MMS-1 and *Magnetococcus* sp. strain MC-1, as well as others. A number of MTB are available in pure culture, including AMB. The doubling time of AMB in pure culture is approximately eight hours and is close to that of a typical mammalian cell.

Standard MTB growth media uses succinic acid as the main carbon source, but MTB can be grown with fumarate, tartrate, malate, lactate, pyruvate, oxaloacetate, malonate, P-hydroxybutyrate and maleate as the sole carbon source. These metabolites are present inside eukaryotic cells. Microaerophillic, facultative anaerobic, and obligate anaerobic MTB strains have been identified. Oxygen concentrations in the cytosol of eukaryotic cells are low due to sequestration by proteins such as myoglobin and concentration in specific cellular locations, e.g., mitochondria, thus the microaerophilic or facultative anaerobic environment necessary for MTB growth is already present in a eukaryotic cell.

MTBs can also be classified by the magnetic particles they synthesize, either magnetite ($Fe_3O_4$) or greigite ($Fe_3S_4$). Magnetite producers are microaerophilic or facultative anaerobic, need some oxygen source for magnetosome synthesis, and have optimal growth temperatures near physiological temperature.

In some embodiments, the single-celled organisms of the invention are genetically modified. Molecular biology tools have been developed for genetic manipulations of MTB most extensively in AMB and *M. gryphiswaldense* strain MSR-1 (reviewed in Jogler, C. and Schtiler, D. in Magnetoreception and Magnetosomes in Bacteria, New York, Springer, 2007 p 134-138 (which is incorporated by reference in its entirety for all purposes)). Since the genome of AMB was the first sequenced of any MTB, all MTB gene references herein refer to this genome unless otherwise specified. The genomes of two other *Magnetospirillum* strains and *Magnetococcus* sp. strain MC-1 have also been recently sequenced. Genes from these strains or other MTB strains, presently culturable or unculturable, sequenced or unsequenced, know or unknown, can be used in the present invention.

The genes responsible for magnetosome formation in MTB cluster in genomic islands, known as the magnetosome island (MAI). In *M. gryphiswaldense*, the 130 kb MAI is generally structured into four polycistronic operons: the mamAB operon has 17 identified ORFs extending over 16.4 kb; the mamGFDC operon has 4 identified ORFs is 2.1 kb and 15 kb upstream of mamAB; the mms6 operon has 6 identified ORFs is 3.6 kb and 368 by upstream of the mamGFDC; the mamXY operon has 4 identified ORFs is located about 30 kb downstream of mamAB; and the monocistronic mamW gene. In the MA1 the proteins: Mam W, Mgl457, Mgl458, Mgl459, Mms6, Mgl462, MamG, MamF, MamD, MamC, MamH, MamI, MamE, MamJ, MamK, MamL, MamM, MamN, MamO, MamP, MamA, MamQ, MamR, MamB, MamS, MamT, MamU, and Mgl505 have been identified, many of which have been given specific functions in magnetosome formation. Four genes outside the MAI have been liked to magnetosome formation, mamY, mtxA, mmsF and mamX. Conserved MAI's have been found in other MTB with some differences in genomic organization and size.

In some embodiments, genetic modifications are made to the single-celled organism. Such modifications can be directed modifications, random mutagenesis, or a combination thereof. Natural endosymbionts are donors of novel metabolic capabilities and derive nutritional requirements from the host.

Natural colonization of a host by the symbionts occurs in seven stages: 1) transmission, 2) entry, 3) countering of host defense, 4) positioning, 5) providing advantage to the host, 6) surviving in host environment, and 7) regulation.

In some embodiments, mutual nutritional dependence (biotrophy) may be established between the single-celled organism and the eukaryotic cell. In one embodiment, the single celled organism comprises at least one deletion of a gene encoding an enzyme for synthesizing an essential molecule, wherein said essential molecule is produced by the eukaryotic host cell. An essential molecule can include, but is not limited to, an amino acid, a vitamin, a cofactor, and a nucleotide. For instance, biotrophy can be accomplished by knocking-out the ability of the single-celled organism to make an amino acid, which will then be derived from the host. Glycine is a reasonable choice as it is highly abundant in mammalian cells and a terminal product in bacterial amino acid biogenesis; at least 22 other possibilities exist. The enzyme serine hydroxymethyltransferase converts serine into glycine at the terminus of the 3-phosphoglycerate biosynthetic pathway for amino acid production. In one embodiment, the single-celled organism is an AMB in which the gene amb2339 (which encodes the enzyme serine hydroxymethyltransferase) is genetically modified. There are numerous methods for mutating or knocking-out genes known to those of ordinary skill in the art, including in vitro mutagenesis, targeted insertion of DNA into the gene of interest by homologous recombination or deletion of the gene (or operon, as most of the genes in the bacteria cluster in operons), or using endonucleases provided appropriate sites only around the target are present in the genome.

In another embodiment, nutritional dependence for a single-celled organism on the host cell could also be established by eliminating the ability of the single-celled organism to synthesize various metabolites, cofactors, vitamins, nucleotides, or other essential molecules.

In some embodiments of the invention, an MTB has mutations and/or deletions in genes associated with mobility and/ or secretion. MTB are flagellated, and in some embodiments of the invention the MTB has a deletion and/or mutation in at least one gene encoding molecular machinery associated with the flagella, such that the magnetic bacterium does not produce a functional flagellum. Additionally, many MTB secrete various compounds, such as hydroxamate and catechol siderophores, which may be detrimental to or elicit an immune response from the host. In the sequenced genome of AMB, of the 4559 ORF's, 83 genes have been related to cell mobility and secretion. The flagellar assembly is known to be composed of the gene products of amb0498, amb0500, amb0501, amb0502, amb0503, amb0504, amb0505, amb0610, amb0614, amb0615, amb0616, amb0617, amb0618, amb0619, amb0628, amb1289, amb1389, amb2558, amb2559, amb2578, amb2579, amb2856, amb3493, amb3494 amb3495, amb3496, amb3498, amb3824, and amb3827. The flagella is controlled by the chemotaxis machinery which is composed of at least the gene products of amb0322, amb0323, amb0324, amb0325, amb0326, amb1806, amb1963, amb1966, amb2333, amb2635, amb2640, amb2648, amb2652, amb2826, amb2932, amb3002, amb3003, amb3004, amb3007, amb3102, amb3329, amb3501, amb3502, amb3654, amb3879, and amb3880.

In one embodiment, genes encoding antibiotic resistance are inserted into the genome of the single-celled organism. Eukaryotic cells cultured in media containing the antibiotic will require the single-celled organism for survival. Neomycin resistance is conferred by either one of two aminoglycoside phosphotransferase genes, which also provide resistance against geneticin (G418), a commonly used antibiotic for eukaryotes. Hygromycin B resistance is conferred by a kinase that inactivates hygromcin B by phosphorylation. Puromycin is a commonly used antibiotic for mammalian cell culture and resistance is conferred by the pac gene encoding puromycin N-acetyl-transferase. External control of the antibiotic concentration allows intracellular regulation of the copy number of the single-celled organism. Any other system where resistance or tolerance to an external factor is achieved by chemical modification of this factor can also be employed. An indirect nutritive advantage on eukaryotic cells may also be established by using MTB and a magnetic culture method. In this embodiment, magnetic fields are established to confer an advantage to eukaryotic cells containing MTB. This could be either by providing the means for attachment to culture matrix or the access to necessary growth or media factors.

In another embodiment, genetic modifications are made the MTB genome to enhance intracellular stability against the host defense mechanisms for a particular host cell type. Many eukaryote endosymbionts and endoparasites, such as the proteobacterial endosymbionts of insects such as *Buchnera, Wigglesworthia*, and *Wolhachia*; the methanogenic endosymbionts of anaerobic ciliates; the nitrogen-fixing symbionts in the diatom *Rhopalodia*; the chemosynthetic endosymbiont consortia of gutless tubeworms (*Olavius* or *Jnanidrillus*), the cyanobacterial endosymbionts of sponges, the endosymbionts of all five extant classes of *Echinodermata*, the *Rhizobia* endosymbionts of plants, various endosymbiotic algae, the *Legionella*-like X bacteria endosymbionts of *Ameoba proteus*, numerous *Salmonella* sp., *Mycobacterium tuberculosis, Legionella pneumophila*, etc. reside in membrane-bound vacuoles often termed symbiosomes, while some species, such as *Blochmannia*, the rickettsia, *Shigella*, enteroinvasive *Escherichia coli*, and *Listeria*, have the ability to inhabit the cytosol. The Dot-Icm Type IV secretory system is employed by many intracellular bacteria acquired by phagocytosis to evade the endocytic pathway and persist in the host cell. This system has been well-studied in *L. pneumophila* and consists of the proteins: DotA through DotP, DotU, DotV, IcmF, IcmQ through IcmT, IcmV, IcmW and IcmX. In *Photorhabdus luminescens*, the luminescent endosymbiont of nematodes, the genes encoding RTX-like toxins, proteases, type III secretion system and iron uptake systems were shown to support intracellular stability and replication. The gene bacA and the regulatory system BvrRS are essential for maintenance of symbiosis between *Rhizobia* and plants as well as the survival of *Brucella ahortus* in mammalian cells. The PrfA regulon enables some *Listeria* species to escape the phagesome and inhabit the cytosol. The desired cellular location (e.g., symbiosome or cytosol) of the intracellular MTB will dictate which genes are required to be expressed in the MTB (either directly from the genome or through a stable vector) for survival and proliferation in the host environment. The endogenous plasmid pMGT is highly stable in MTB and a number of other broad range vectors (those ofIncQ, IncP, pBBR1, etc.) are capable of stable replication in MTB.

In another embodiment, the single-celled organism is genetically modified by knocking in genes, such as bacteriostatic gene(s), siderophore gene(s), metabolic requirement gene(s), suicide gene(s), life cycle regulation gene(s), transporter gene(s), and escape from the phagosome gene(s). In another embodiment, the single-celled organisms are randomly mutated and subsequently screened for enhanced integration within the host cell. Random mutation can be accomplished by treatment with mutagenic compounds, exposure to UV-light or other methods know to those skilled in the art.

In another embodiment, transgenetic modification(s) are made to counter eukaryotic cell defenses using genes from various parasites or endosymbionts. In another embodiment, the population of the single-celled organisms in the eukaryotic host cell is regulated though a balance of intrinsic use of host mechanisms (nutrient availability, control of reproduction, etc.) and antibiotic concentration.

In another embodiment, a natural endosymbiont or an intracellular parasite is genetically modified to produce magnetosomes. Endosymbionts of insects such as *Buchnera, Wigglesworthia*, and *Wolbachia*; the methanogenic endosymbionts of anaerobic ciliates; the nitrogen-fixing symbionts in the diatom *Rhopalodia*; the chemosynthetic endosymbiont consortia of gutless tubeworms (*Olavius* or *Inanidrillus*), the cyanobacterial endosymbionts of sponges, the endosymbionts of all five extant classes of *Echinodermata*, the *Rhizobia* endosymbionts of plants, various endosymbiotic algae, the *Legionella*-like X bacteria endosymbionts of *Ameoba proteus*, numerous *Salmonella* sp., *Mycobacterium tuberculosis, Legionella pneumophila* belong to α-proteobacteria and could be genetically engineered to produce magnetosomes. In another embodiment, a pre-existing organelle can be genetically modified to express one or more magnetosome genes to produce an artificial endosymbiont. For instance, mitochondria, plastids, hydrogenosomes, apicoplasts or other organelles, which harbor their own genetic material, can be genetically altered.

In a preferred embodiment, the single-celled organism is an MTB, which may or may not be genetically altered, that produces magnetic particles upon culturing of the eukaryotic cells.

Eukaryotic Cells

The invention provides eukaryotic cells comprising single-celled organisms in the eukaryotic cells that are heritable and methods of introducing the single-celled organisms into host cells.

In some embodiments the eukaryotic cells are plant cells. In some embodiments the eukaryotic cells are cells of monocotyledonous or dicotyledonous plants including, but not limited to, maize, wheat, barely, rye, oat, rice, soybean, peanut, pea, lentil and alfalfa, cotton, rapeseed, canola, pepper, sunflower, potato, tobacco, tomato, eggplant, eucalyptus, a tree, an ornamental plant, a perennial grass, or a forage crop. In other embodiments the eukaryotic cells are algal, including but not limited to algae of the genera *Chlorella, Chlamydomonas, Scenedesmus, Isochrysis, Dunaliella, Tetraselmis, Nannochloropsis*, or *Prototheca*, In some embodiments the eukaryotic cells are fungi cells, including but not limited to fungi of the genera *Saccharomyces, Klyuveromyces, Candida, Pichia, Debaromyces, Hansenula, Yarrowia, Zygosaccharomyces*, or *Schizosaccharomyces*.

In some embodiments the eukaryotic cells of the invention are animal cells. In some embodiments the eukaryotic cells are mammalian, such as mouse, rat, rabbit, hamster, human, porcine, bovine, or canine. Mice routinely function as a model for other mammals, most particularly for humans. (See, e.g., Hanna, J., Wernig, M., Markoulaki, S., Sun, C., Meissner, A., Cassady, J. P., Beard, C., Brambrink, T., Wu, L., Townes, T. M., Jaenisch, R. Treatment of sickle cell anemia mouse model with iPS cells generated from autologous skin. *Science* 318: 1920-1923 (2007); Holtzman, D. M., Bales, K. R., Wu, S., Bhat, P., Parsadanian, M., Fagan, A., Chang, L. K., Sun, Y., Paul, S. M. Expression of human apolipoprotein E reduces amyloid-β deposition in a mouse model of Alzheimer's disease. *J. Clin. Invest.* 103(6): R15-R21 (1999); Warren, R. S., Yuan, H., Matli, M. R., Gillett, N. A., Ferrara, N. Regulation by vascular endothelial growth factor of human colon cancer tumorigenesis in a mouse model of experimental liver metastasis. *J. Clin. Invest.* 95: 1789-1797 (1995) (each of these three publications is incorporated by reference in its entirety for all purposes)).

In some embodiments, the eukaryotic cell is a human cancer cell. There are many human cancer cell lines that are well known to those of ordinary skill in the art, including common epithelial tumor cell lines such as Coco-2, MDA-MB231 and MCF7, non-epithelial tumor cell lines, such as HT-1080 and HL60, the NCI60-cell line panel (see, e.g., Shoemaker, R., The NCI60 human tumor cell line anticancer drug screen. *Nature Reviews Cancer* 6, 813-823 (2006) (which is incorporated by reference in its entirety for all purposes)). Additionally, those of ordinary skill in the art are familiar with obtaining cancer cells from primary human tumors.

In other embodiments, the eukaryotic cells are stem cells. Those of ordinary skill in the art are familiar with a variety of stem cell types, including Embryonic Stem Cells, Inducible Pluripotent Stem Cells, Hematopoietic Stem Cells, Neural Stem Cells, Epidermal Neural Crest Stem Cells, Mammary Stem Cells, Intestinal Stem Cells, Mesenchymal stem cells, Olfactory adult stem cells, and Testicular cells.

In an embodiment, the eukaryotic cell is a cell found in the circulatory system of a human host. For example, red blood cells, platelets, plasma cells, T-cells, natural killer cells, or the like, and precursor cells of the same. As a group, these cells are defined to be circulating host cells of the invention. The present invention may be used with any of these circulating cells. In an embodiment, the eukaryotic host cell is a T-cell. In another embodiment, the eukaryotic cell is a B-cell. In an embodiment the eukaryotic cell is a neutrophil. In an embodiment, the eukaryotic cell is a megakaryocyte.

In another embodiment, at least one gene from the eukaryotic cell is genetically altered. In some embodiments, mutual nutritional dependence (biotrophy) may be established between the artificial endosymbiont and the eukaryotic cell by genetic modification of the eukaryotic cell, using the appropriate molecular biology techniques specific to the target host cell type known to those of ordinary skill in the art, creating eukaryotic cell dependence on the single-celled organism for some essential macromolecule thus establishing the environmental pressures for biotrophy. In another embodiment, nutritional dependence for a single-celled organism on the eukaryotic cell may be established by genetically altering the eukaryotic cell to eliminate the ability of the single-celled organism to synthesize various metabolites, cofactors, vitamins, nucleotides, or other essential molecules. In such embodiments, the essential molecule may be provided by the single-celled organism. In another embodiment, the eukaryotic cell gene encoding the enzyme serine hydroxymethyltransferase, which converts serine into glycine at the terminus of the 3-phosphoglycerate biosynthetic pathway for amino acid production, may be modified.

Methods of Introducing Single-Celled Organisms into Eukaryotic Cells

The single-celled organisms of the invention can be introduced into eukaryotic cells by a number of methods known to those of skill in the art including, but not limited to, microinjection, natural phagocytosis, induced phagocytosis, macropinocytosis, other cellular uptake processes, liposome fusion, erythrocyte ghost fusion, electroporation, receptor mediated methods, and the like. (See Microinjection and Organelle Transplantation Techniques, Celis et al. Eds.; Academic Press: New York, 1986 and references therein, (incorporated by reference in its entirety for all purposes)).

In one embodiment, a single-celled organism is introduced to the host cell by microinjection into the cytoplasm of the host cell. A variety of microinjection techniques are known to those skilled in the art. Microinjection is the most efficient of transfer techniques available (essentially 100%) and has no cell type restrictions (Id.; Xi, Z. & Dobson, S. Characterization of *Wolbachia* transfection efficiency by using microinjection of embryonic cytoplasm and embryo homogenate. *Appl. Environ. Microbiol.* 71(6): 3199-3204 (2005); Goetz, M., Bubert, A., Wang, G., Chico-Calero, I., Vazquez-Boland, J. A., Beck, M., Slaghuis, J., Szalay, A. A., Goebel, W. Microinjection and growth of bacteria in the cytosol of mammalian host cells. *Proc. Natl. Acad Sci USA* 98:12221-12226 (2001) (each of these three publications is incorporated by reference in its entirety for all purposes)).

Naturally phagocytotic cells have been show to take up bacteria, including MTB (Burdette, D. L., Seemann, J., Orth, K. Vibrio VopQ induces PI3-kinase independent autophagy and antagonizes phagocytosis. *Molecular microbiology* 73: 639 (2009); Wiedemann, A., Linder, S., Grassi, G., Albert, M., Autenrieth, I., Aepfelbacher, M. *Yersinia enterocolitica* invasin triggers phagocytosis via β1 integrins, CDC42Hs and WASp in macrophages. *Cellular Microbiology* 3: 693 (2001); Hackam, D. J., Rotstein, O. D., Schreiber, A., Zhang, W., Grinstein, S. Rho is required for the initiation of calcium signaling and phagocytosis by Fcγ receptors in macrophages. *J. of Exp. Med.* 186(6): 955-966 (1997); Matsunaga, T., Hashimoto, K., Nakamura, N., Nakamura, K., Hashimoto, S. Phagocytosis of bacterial magnetite by leucocytes. *Applied Microbiology and Biotechnology* 31(4): 401-405 (1989) (each of these four publications is incorporated by reference in its entirety for all purposes)).

This method is scalable, but may be limited to specific cell types (e.g., macrophage). However, recent studies have shown that non-phagocytotic cell types can be induced to endocytose bacteria when co-cultured with various factors: media and chemical factors, biologic factors (e.g., baculovirus, protein factors, genetic knock-ins, etc.). (See, e.g., Salminen, M., Airenne, K. J., Rinnankoski, R., Reimari, J., Valilehto, O., Rinne, J., Suikkanen, S., Kukkonen, S., Yla- Herttuala, S., Kulomaa, M. S., Vihinen-Ranta, M. Improvement in nuclear entry and transgene expression of baculoviruses by disintegration of microtubules in human hepatocytes. *J. Virol.* 79(5): 2720-2728 (2005); Modalsli, K. R., Mikalsen, S., Bukholm, G., Degre, M. Microinjection of HEp-2 cells with coxsackie B1 virus RNA enhances invasiveness of *Shigella flexneri* only after prestimulation with UV-inactivated virus. *APMIS* 101: 602-606 (1993); Hayward, R. D. & Koronakis, V. Direct nucleation and bundling of actin by the SipC protein of invasive *Salmonella. The EMBO Journal* 18: 4926-4934 (1999); Yoshida, S., Katayama, E., Kuwae, A., Mimuro, H., Suzuki, T., Sasakawa, C. *Shigella* deliver an effector protein to trigger host microtubule destabilization, which promotes Rac1 activity and efficient bacterial internalization. *The EMBO Journal* 21: 2923-2935 (2002); Bigildeev et al. *J. Exp Hematol.*, 39: 187 (2011); Finlay, B. B. & Falkow, S. Common themes in microbial pathogenicity revisited. *Microbiol. and Mol. Biol. Rev.* 61: 136-169 (1997) (each of these six publications is incorporated by reference in its entirety for all purposes).

The related process, macropinocytosis or "cell drinking," is a method numerous bacteria and viruses employ for intracellular entry (Zhang (2004) In: Molecular Imaging and Contrast Agent Database (MICAD) [database online]; Bethesda (MD): National Library of Medicine (US), NCBI; 2004-2011 (each of these two publications is incorporated by reference in its entirety for all purposes)). Various protocols exist which can be employed to induce cells to take up bacteria. Several agents, such as nucleic acids, proteins, drugs and organelles have been encapsulated in liposomes and delivered to cells (Ben-Haim, N., Broz, P., Marsch, S., Meier, W., Hunziker, P. Cell-specific integration of artificial organelles based on functionalized polymer vesicles. *Nano Lett.* 8(5): 1368-1373 (2008); Lian, W., Chang, C., Chen, Y., Dao, R., Luo, Y., Chien, J., Hsieh, S., Lin, C. Intracellular delivery can be achieved by bombarding cells or tissues with accelerated molecules or bacteria without the need for carrier particles. *Experimental Cell Research* 313(1): 53-64 (2007); Heng, B. C. & Cao, T. Immunoliposome-mediated delivery of neomycin phosphotransferase for the lineage-specific selection of differentiated/committed stem cell progenies: Potential advantages over transfection with marker genes, fluorescence-activated and magnetic affinity cell-sorting. *Med. Hypotheses* 65(2): 334-336 (2005); Potrykus (1990) Ciba Found Symp, Vol. 1 54: 198 (each of these four publications is incorporated by reference in its entirety for all purposes)). This method is inexpensive, relatively simple and scalable. Additionally, liposome uptake can be enhanced by manipulation of incubation conditions, variation of liposome charge, receptor mediation, and magnetic enhancement. (See, e.g., Pan et al. *Int. J. Pharm.* 358: 263 (2008); Sarbolouki, M. N. & Toliat, T. Storage stability of stabilized MLV and REV liposomes containing sodium methotrexate (acqueous & lyophilized). *J. Pharm. Sci. Techno.*, 52(10): 23-27 (1998); Elorza, B., Elorza, M. A., Sainz, M. C., Chantres, J. R. Comparison of particle size and encapsulation parameters of three liposomal preparations. I Microencapsul. 10(2): 237-248 (1993); Mykhaylyk, O., Sánchez-Antequera, Y., Vlaskou, D., Hammerschmid, E., Anton, M., Zelphati, O. and Plank, C. Liposomal Magnetofection. *Methods Mol. Bio.*, 605: 487-525 (2010) (each of these four publications is incorporated by reference in its entirety for all purposes)).

Erythrocyte-mediated transfer is similar to liposome fusion and has been shown to have high efficiency and efficacy across all cell types tested (Microinjection and Organelle Transplantation Techniques; Celis et al. Eds.; Academic Press: New York, 1986 (which is incorporated by reference in its entirety for all purposes)). Typically erythrocytes are loaded by osmotic shock methods or electroporation methods (Schoen, P., Chonn, A., Cullis, P. R., Wilschut, J., and Schuerrer, P. Gene transfer mediated by fusion protein hemagglutinin reconstituted in cationic lipid vesicles. *Gene Therapy* 6: 823-832 (1999); Li, L. H., Hensen, M. L., Zhao, Y. L., Hui, S. W. Electrofusion between heterogeneous-sized mammalian cells in a pellet: potential applications in drug delivery and hybridoma formation. *Biophysical Journal* 71:479-486 (1996); Carruthers, A., & Melchior, D. L. A rapid method of reconstituting human erythrocyte sugar transport proteins. Biochem. 23: 2712-2718 (1984) (each of these three publications is incorporated by reference in its entirety for all purposes). Alternatively, erythrocytes may be loaded indirectly by loading hematopoietic progenitors with single-celled organisms and inducing them to differentiate and expand into erythrocytes containing single-celled organisms.

Electroporation is a commonly used, inexpensive method to deliver factors to cells. (Potrykus, I. Gene transfer methods for plants and cell cultures. *Ciba Found Symp* 154, 198-208; discussion 208-112 (1990); Wolbank, S. et al. Labeling of human adipose-derived stem cells for non-invasive in vivo cell tracking. *Cell Tissue Bank* 8, 163-177 (2007) (each of these two publications is incorporated by reference in its entirety for all purposes)).

In another embodiment, a eukaryotic cell that naturally endocytoses bacteria (e.g., Chinese hamster ovary (CHO)) is used. In one embodiment, the modified single-celled bacteria are added to the CHO culture directly. CHO cells are cultured by standard procedures in Ham's F-12 media with 10% fetal calf serum media prior to infection with the MTB. Post infection, the media is augmented with additional iron (40 to 80 µM) as either ferric malate or $FeCl_3$. Numerous other cell types internalize bacteria by endocytosis or more specifically phagocytosis; endosymbionts or parasites have their own methods for cellular entry and these natural processes can be exploited for internalization of the artificial endosymbionts resulting in the generation of so-called symbiosomes. In another embodiment, symbiosomes from one cell can be transplanted to another cell type (i.e., one incapable of endocytosis of artificial endosymbionts) using microinjection, organelle transplantation, and chimera techniques. These host cells are cultured in typical media and with the techniques for the specific cell type.

In one embodiment, a single-celled organism is introduced to the host cell by a liposome mediated process. Mitochondria and chloroplasts, which are larger than MTB, have been efficiently introduced into eukaryotic cells when encapsulated into liposomes. (Bonnett, H. T. *Planta* 131, 229 (1976); Giles, K.; Vaughan, V.; Ranch, J.; Emery, J. Liposome-mediated uptake of chloroplasts by plant protoplasts. *In Vitro Cellular & Developmental Biology—Plant* 16(7) 581-584 (each of these two publications is incorporated by reference in its entirety for all purposes)). Numerous liposome fusion protocols and agents are available and can be used by the skilled artisan without undue experimentation. (See, e.g., Ben-Haim, N., Broz, P., Marsch, S., Meier, W., Hunziker, P. Cell-specific integration of artificial organelles based on functionalized polymer vesicles. *Nano Lett.* 8(5): 1368-1373 (2008); Lian, W., Chang, C., Chen, Y., Dao, R., Luo, Y., Chien, J., Hsieh, S., Lin, C. Intracellular delivery can be achieved by bombarding cells or tissues with accelerated molecules or bacteria without the need for carrier particles. *Experimental Cell Research* 313(1): 53-64 (2007); Heng, B. C. & Cao, T. Immunoliposome-mediated delivery of neomycin phosphotransferase for the lineage-specific selection of differentiated/committed stem cell progenies: Potential advantages over transfection with marker genes, fluorescence-activated and magnetic affinity cell-sorting. *Med. Hypotheses* 65(2): 334-336 (2005); Potrykus (1990) Ciba Found Symp, Vol. 1 54: 198 (each of these four publications is incorporated by reference in its entirety for all purposes)).

Methods of Use of Eukaryotic Cells Comprising Single-Celled Organisms

This invention provides methods of using phenotypes introduced into eukaryotic cells by single-celled organisms of the invention. In some embodiments, the phenotype used is a heritable functionality not otherwise present in the eukaryotic cells. In some embodiments, eukaryotic cells with a magnetic phenotype are magnetically manipulated.

In some embodiments eukaryotic cells of the invention with magnetic phenotypes can be detected and monitored using magnetic detection or imaging techniques such as magnetic resonance imaging (MRI). MRI is a widely used clinical diagnostic tool because it is non-invasive, allows views into optically opaque subjects (including mice, humans, and other mammals), and provides contrast among soft tissues at reasonably high spatial resolution, compared to non-magnetic imaging (such as optical probes) which tend to have low special resolution and to be limited in penetration depth. Conventional MRI focuses almost exclusively on visualizing anatomy and has no specificity for any particular cell type. The 'probe' used by conventional MRI is the ubiquitous proton $^1H$ in mobile water molecules. Contrast agents can be used for cell-type specificity, but contrast agents dilute or have toxicology issues, and can only be used for short-term studies. Some embodiments of this invention facilitate cell-specific MRI imaging in living subjects for longer-term studies.

In some embodiments, eukaryotic cells of the invention with magnetic phenotypes are mammalian cancer cells such as human cancer cell line NCI 60, other human cancer cell lines, murine cancer cells lines, or canine cancer cell lines. These magnetic cancer cells can be injected into immunocompromised mammals such as mice and can then be monitored with magnetic imaging to track tumor progression over time. In some embodiments, anti-cancer treatments or putative treatments may be provided to the immunocompromised mammal during the period that tumor progression is being tracked in real time. In some embodiments, viability of eukaryotic cells of the invention with magnetic phenotypes is monitored using MRI to assess in vivo cell response to different conditions, including drug treatments.

In some embodiments, eukaryotic cells of the invention with magnetic phenotypes are metastatic cancer cells that are introduced into experimental animals by methods including injection. MRI can then be used to monitor the process of metastasis and movement of metastatic cancer cells throughout the experimental animals. In some embodiments magnetic eukaryotic cancer cells of the invention are injected into a tumor bearing mammal, such as a mouse, and MRI is used to track metastatic cell circulation through the mammal.

In some embodiments, eukaryotic cells of the invention with magnetic phenotypes are macrophages and are injected into experimental animals. Magnetic imaging is used to detect any aggregations of macrophages within the animals. Macrophages aggregate to the sites of inflammation, which can be caused by malignant lesions including metastasis.

In some embodiments, eukaryotic cells of the invention with magnetic phenotypes are stem cells or were derived from stem cells, including ES cells, iPS cells, or adult stem cells obtained from mammalian species including but not limited to human, mouse, rat, and pig. Stem cells may be introduced into a target organism directly or may be first differentiated in vitro and then introduced into a target organism. The in vivo fate, including localization, growth rates and viability, of the introduced cells can be assayed through magnetic imaging.

In some embodiments, eukaryotic cells of the invention with magnetic phenotypes are hematopoietic stem or progenitor cells, which are then introduced into a mammal. When hematopoietic stem or progenitor cells are introduced into mammals, these cells will reside in the bone marrow. The behavior of the magnetic hematopoietic stem or progenitor cells, including their localization, proliferation and mobilization into blood stream upon receiving different stimuli, can be monitored through magnetic imaging.

In some embodiments, magnetic artificial endosymbionts divide more slowly than stem cell host cells in which they reside. Over time, stem cells, which generally divide more slowly than more differentiated progenitor cells, will retain magnetic phenotype longer than more differentiated progenitor cells and the two types of cells will become measurably district when imaged magnetically. In some embodiments, eukaryotic cells of the invention with magnetic phenotypes are fused to a eukaryotic cell line of a desired cell type, creating chimeric calls. Chimeric cells can be introduced into an animal and tracked by magnetic imaging.

In some embodiments, eukaryotic cells of the invention with magnetic phenotypes are embryonic cells. In some embodiments the embryonic cells are fertilized animal eggs, such as mouse or rat. In some embodiments, embryos are implanted into female animals and allowed to develop, leading to the production of animals with cells containing single-celled organism throughout their bodies. Magnetic tissues can be harvested from the resulting organisms and magnetic cell lines can be derived from them. In some embodiments, these animals are bred and the magnetic phenotype is inherited maternally. In some embodiments, eukaryotic cells of the invention with magnetic phenotypes are introduced into multi-celled embryos. The cell lineage of the magnetic cell can be tracked by magnetic imagine as the embryo develops.

In some embodiments, eukaryotic cells of the invention with magnetic phenotypes are moved by magnetically attracting the eukaryotic cells. In some embodiments, this movement is achieved using externally generated magnetic fields and field gradients. Various devices have been reported for magnetic targeting, such as those in U.S. Pat. No. 8,159,224 and Riegler J, Liew A, Hynes S O, Ortega D, O'Brien T, Day R M, Richards T, Sharif F, Pankhurst Q A, Lythgoe M F. Superparamagnetic iron oxide nanoparticle targeting of MSCs in vascular injury. Biomaterials. 2013 March; 34(8): 87-94 In some embodiments, eukaryotic cells of the invention with magnetic phenotypes are separated from a heterogeneous population of non-magnetic cells, either in vitro or in vivo (following introduction into an organism) by using a magnet to attract the magnetic cells.

In some embodiments, eukaryotic cells of the invention with magnetic phenotypes are introduced into the bloodstream or other fluids of a target organism. The eukaryotic cells can be directed to an area of interest on the organism and localized there with an aid of a magnet positioned adjacent to this area. In some embodiments, the eukaryotic cells can be stem cells that are directed to and held in an area on a mammal's body where they could have therapeutic effect. In some embodiments, the eukaryotic cells can be immune cells which can be directed to a particular location on a mammal's body, including to a tumor or injury site. In some embodiments, the eukaryotic cells can be loaded with a therapeutic agent that can be released after being magnetically directed to a desired area.

In some embodiments, eukaryotic cells of the invention with magnetic phenotypes are placed in an alternating magnetic field, or alternative magnetic field, referred to as an AMF, for a technique called Magnetic Hyperthermia Technique (MHT). AMF and MHT are described in U.S. Publication No. US20120302819 (U.S. application Ser. No. 13/510, 416), and in Silva A C, Oliveira T R, Mamani J B, Malheiros S M, Malavolta L, Pavon L F, Sibov T T, Amaro E Jr, Tannús A, Vidoto E L, Martins M J, Santos R S, Gamarra L F. Application of hyperthermia induced by superparamagnetic iron oxide nanoparticles in glioma treatment. Int J. Nanomedicine. 2011; 6:591-603 (both of which are incorporated by reference in its entirety for all purposes). Hyperthermia is a therapeutic procedure that promotes the increase of temperature in body tissues in order to change the functionality of the cellular structures. Its activity is based on the fact that a temperature increase can induce cell damaged, including cell lysing and cell death. In some embodiments, the eukaryotic cells of the invention are subjected to an AMF for 10, 20, 30, 40, 50, 60, 70, 80, or 90 minutes. In some embodiments, magnetic field frequencies of an applied AMF lie between 50 kHz and 1 MHz. In some embodiments, the magnetic field amplitude of an applied AMF remains below 100 mTln. In some embodiments, the eukaryotic cells of the invention subjected to MHT are tumor cells, which are less resistant to sudden increases in temperature than the normal surrounding cells. In some embodiments, the eukaryotic cells of the invention are tumor cells or are next to tumor cells and are subjected to an alternating magnetic field until the internal temperature of the tumor reached between 43 degrees Celsius and 47 degrees Celsius.

In some embodiments, eukaryotic cells of the invention with magnetic phenotypes are placed in a spinning magnetic field, resulting in rotation of the single-celled organisms inside the cells and cell damage, including cell lysing and death. In some embodiments, eukaryotic cells of the invention with magnetic phenotypes in a heterogeneous population of non-magnetic cells are selectively damaged by subjecting the entire cell population to an alternating magnetic field or to a spinning magnetic field. In some embodiments, eukaryotic cells of the invention with magnetic phenotypes in a heterogeneous population of non-magnetic cells are placed in an alternating magnetic field or a spinning magnetic field, resulting in damage to both the eukaryotic cells of the invention and the non-magnetic cells located near the cells of the invention. In some embodiments, eukaryotic cells of the invention with magnetic phenotypes are introduced into an animal and are targeted to a location within the animal by magnetic manipulation or other forms of cell targeting known in the art. The location within the animal can then be subjected to an alternating magnetic field or a spinning magnetic field, resulting in the damage to cells surrounding the magnetic cells. In some embodiments, eukaryotic cells of the invention with magnetic phenotypes are introduced into an animal and are localized to a tumor site within the animal by magnetic manipulation or other forms of cell targeting known in the art. The tumor can then be subjected to an alternating magnetic field or a spinning magnetic field, resulting in the damage to tumor cells surrounding the magnetic cells. In some embodiments, eukaryotic cells of the invention with magnetic phenotypes are stem cells, including ES cells, iPS cells, or adult stem cells obtained from mammalian species including but not limited to human, mouse, rat, and pig. Stem cells may be introduced into a target organism directly or may be first differentiated in vitro and then introduced into a target organism. Following introduction, the animal can be subjected to an alternating magnetic field or a spinning magnetic field, resulting in the death of introduced stem cells and resulting lineages of these stem cells. The in vivo fate, including localization, growth rates and viability, of the introduced cells can be assayed through magnetic imaging.

The inventions disclosed herein will be better understood from the experimental details which follow. However, one skilled in the art will readily appreciate that the specific methods and results discussed are merely illustrative of the inventions as described more fully in the claims which follow thereafter.

EXAMPLES

Example 1

Microinjection of gfp⁺AMB into Murine Cells

A. Construction of gfp⁺AMB.

Expression vectors for eGFP, one including a Shine-Dalgarno sequence upstream of the gfp gene and one without a Shine Dalgarno, sequence were cloned into cryptic broad host range vector pBBR1MCS-2 (Kovach, M. E., et al. Four new derivatives of the broad-host-range cloning vector pBBR1MCS, carrying different antibiotic-resistance cassettes. *Gene* 166, 175-176, (1995) (which is incorporated by reference in its entirety for all purposes)). AMB (ATCC 700264) was transformed with this construct. (Matsunaga, T. et al. Complete genome sequence of the facultative anaerobic magnetotactic bacterium *Magnetospirillum* sp. strain AMB-1. DNA Res. 12, 157-166 (2005); Burgess J. G., et al. Evolutionary relationships among Magnetospirillum strains inferred from phylogenetic analysis of 16S rDNA sequences. *J. Bacteriol.* 175: 6689-6694 (1993); Matsunaga T, et al. Gene transfer in magnetic bacteria: transposon mutagenesis and cloning of genomic DNA fragments required for magnetosome synthesis. *J. Bacteriol.* 174: 2748-2753 (1992); Kawaguchi R, et al. Phylogeny and 16s rRNA sequence of Magnetospirillum sp. AMB-1, an aerobic magnetic bacterium. *Nucleic Acids Res.* 20: 1140, (1992) (each of these four publications is incorporated by reference in its entirety for all purposes)).

Transformation was achieved by conjugation using a donor *Escherichia coli* strain as described by Goulian, M. van der Woude, M. A. A simple system for converting lacZ to gfp reporter fusions in diverse bacteria. *Gene* 372, 219-226 (2006); Scheffel, A. Schiller, D. The Acidic Repetitive Domain of the Magnetospirillum gryphiswaldense MamJ Protein Displays Hypervariability but Is Not Required for Magnetosome Chain Assembly. *J. Bacteriol.* September; 189 (17): 6437-6446 (2007) (each of these two publications is incorporated by reference in its entirety for all purposes). The mating reactions were cultured for 10 days under defined microaerophilic conditions in the absence of DAP to select for positive transformants.

Following conjugation, gfp⁺AMB transformants with and without the Shine-Dalgarno sequence successfully displayed GFP fluorescence. The tranformants containing the Shine-Dalgarno sequence displayed higher levels of GFP fluorescence than the transformants without this sequence. The resulting fluorescence did not leave the gfp⁺AMB cells when viewed at 100× magnification at 488 nm excitation.

The magnetic properties of the gfp⁺AMB were analyzed by MRI. The gfp⁺AMB was suspended in agar plugs using a 1.5 T instrument to optimize and characterize the imaging properties. FIG. 1 shows the positive contrast generated with a $T_1$ pulse sequence over a log scale concentration up to ~$10^8$ MTB/mL. Signal intensity was related to concentration.

B. Microinjection into Murine Embryonic Cells.

The gfp+AMB was mircoinjected into one cell of each of 170 mouse embryos at the 2-cell stage. Six concentrations over a log scale up to ~$10^5$ gfp+AMB were injected per cell, estimated by the optical density at 565 nm. Death rate of cells following microinjection was constant across the different injected concentrations. Images overlaying fluorescent and differential interference contrast (DIC) images of cells injected with the highest concentration ($10^5$ MTB/cell) were compared. An uninjected control exhibited low levels of autofluorescence. Slices at different horizontal planes in 8-cell embryos at a given time point were compared. In each embryo, all four cells derived from the injected cell showed significant fluorescence while none of the four cells derived from the uninjected internal controls displayed significant fluorescence.

Figure 2:
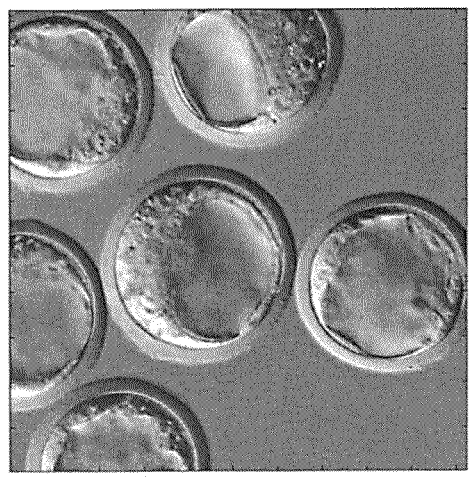
FIG. 2 shows a blastula stage mouse embryo that has had one of its two cells at the 2-cell embryo stage microinjected with gfp+AMB. The embryo is imaged with Leica SP2 AOBS spectral confocal inverted microscope surrounded by an environmental control chamber for live-cell imaging with 20×, 0.7 NA objective, and optical zoom of 3×. Panel A shows differential interference contrast (DIC) image and Panel B shows a gray scale fluorescence capture of the same image.
Figure 2:
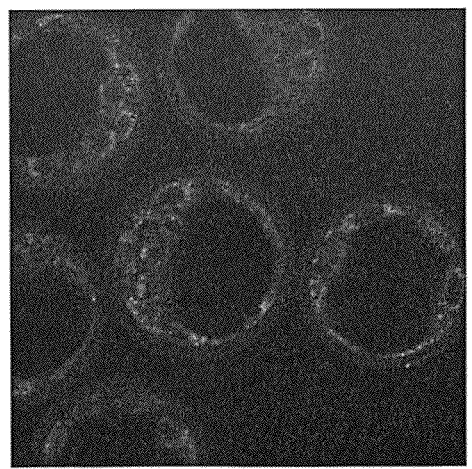

The embryos were allowed to develop for three days after the injection. In each concentration level, embryos survived for up to the full three days developing to the 256 cell blastula stage and appeared healthy enough for implantation. Numerous cells within each blastula displayed significant fluorescence, demonstrating that the artificial endosymbionts were transferred to daughter cells across multiple cell divisions as the embryos comprising the eukaryotic host cells developed to the blastula stage. One such blastula is shown in FIG. 2, where Panel A shows a differential interference contrast (DIC) image of the blastula and Panel B) shows a gray scale fluorescence capture of the same image, showing fluorescence in numerous cells throughout the blastula.

Figure 3:
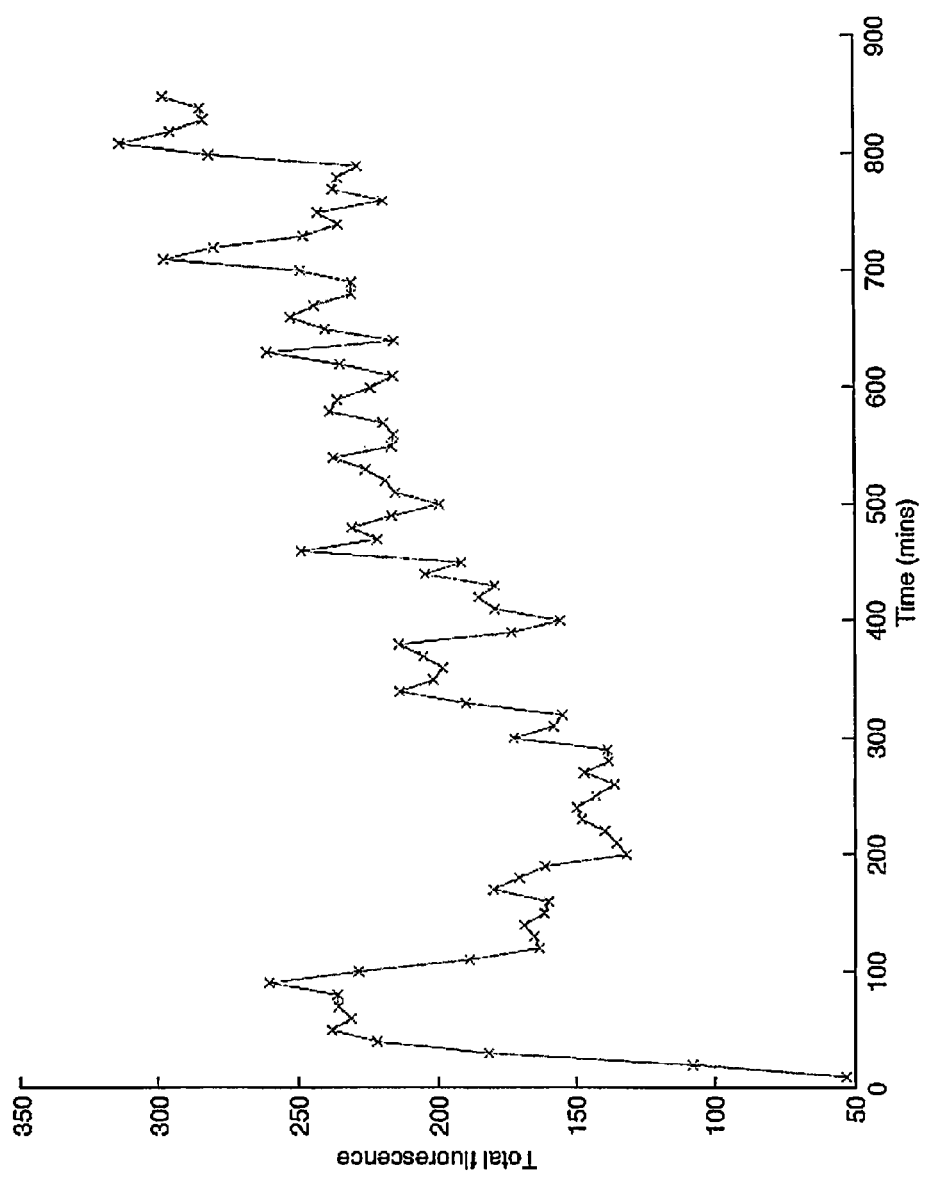
FIG. 3 shows the change of total embryo GFP fluorescence of four mouse embryos over time as measured by confocal microscopy. One of the two cells from the 2-cell stage of each embryo had been microinjected with gfp+AMB, and the total GFP fluorescence of each embryo was measured beginning at the 8-cell stage, 24 hours after microinjection.

Confocal microscopy was used to quantify total expression of GFP throughout four individual embryos by measuring total GFP fluorescence in the entire embryo over time at various points beginning at the eight cell stage of the embryo. FIG. 3 shows the change of embryo fluorescence over time. This indicates that the copy number of artificial endosymbionts was maintained in daughter cells for at least seven generations, such that the fluorescent phenotype of the host cells was maintained as the embryo progressed from the 2-cell stage to the 256-cell blastula stage.

These results demonstrate that, when delivered by microinjection, gfp+AMB were not immediately cleared or degraded and were not toxic to the developing embryo over the course of the three day experiment. Microinjected embryos divided normally, suggesting that gfp+AMB do not display pathogenic markers or secret toxic compounds. They were transferred to daughter cells across many cell divisions, were contained in the cytoplasm, were punctate and well distributed, and maintained copy number within the daughter host cells, such that the fluorescent phenotype of the eukaryote host cells was maintained in daughter cells through at least seven generations. These results demonstrate that AMB can be stably maintained intracellularly and are transferred to daughter cells over at least seven cell divisions.

Example 2

Phagocytic Entry of AMB

Receptor mediated: The inlAB gene is amplified from *L. monocytogenes* genomic DNA (ATCC 19114) and is inserted into pBBR1MCS-5,107 the gentamicin cognate of pBBR1MCS-2 (Kovach, M. E., et al. Four new derivatives of the broad-host-range cloning vector pBBR1MCS, carrying different antibiotic-resistance cassettes. Gene 166, 175-176, (1995)), and gfp+inlAB+AMB is generated. The gfp+inlAB+ AMB is co-cultured with eukaryotic host cells, including common epithelial tumor cell lines Coco-2, MDA-MB231 and MCF7, non-epithelial tumor cell lines, such as HT-1080 and HL60, and murine stem cells. Fluorescent microscopy and FACS are used to monitor and quantify internalization and intracellular location.

Expression of pore-forming haemolysin (hlyA) in AMB is achieved through amplification of hlyA from *L. monocytogenes* genomic DNA (ATCC 19114). The amplified hlyA is inserted into pBBR1MCS-3 (the tetracycline cognate of pBBR1MCS-2) which is then used to transform gfp+AMB. The resulting AMB strain is exposed to murine macrophage cell line J774, capable of spontaneous phagocytosis. Gentomycin treatment is used to eliminate bacteria not internalized and hlyA⁻ AMB is used as negative control. Fluorescent microscopy is used to monitor the intracellular fate and localization of AMB.

If bacteria remain confined to the phagosomes, two genes, plcA and plcB, implicated in escape of *L. monocytogenes* into the cytosol, are introduced. (Smith, G. A., Marquis, H., Jones, S., Johnston, N. C., Portnoy, D. A., Goldfine, H. *Infection and immunity* 63: 4231 (1995); Camilli, A.; Goldfine, H.; Portnoy, D. A. *The Journal of Experimental Medicine* 173: 751 (1991) (each of these two publications is incorporated by reference in its entirety for all purposes)). If bacteria escape successfully, but fail to propagate, hpt is introduced. (Goetz, M., Bubert, A., Wang, G., Chico-Calero, I., Vazquez-Boland, J. A., Beck, M.; Slaghuis, J., Szalay, A. A., Goebel, W. *Proc Natl Acad Sci USA* 98: 12221 (2001); Chico-Calero, I., Suarez, M., Gonzalez-Zorn, B., Scortti, M., Slaghuis, J., Goebel, W., Vazquez-Boland, J. A. *Proc Natl Acad Sci USA* 99: 431 (2002) (each of these two publications is incorporated by reference in its entirety for all purposes)). In *L. monocytogenes*, hpt encodes the transporter responsible for uptake of glucose-6-phosphate from the cytosol. Other genes from *L. monocytogenes* have been implicated in sustaining growth within host (glnA and gltAB and argD) and these are systematically introduced as needed. (Joseph, B., Przybilla, K., Stuhler, C., Schauer, K., Slaghuis, J., Fuchs, T. M., Goebel, W. *Journal of Bacteriol.* 188: 556 (2006) (which is incorporated by reference in its entirety for all purposes)).

Example 3

Regulation of AMB Growth

Regulation of AMB growth in embryonic stem cells can be regulated as follows. Coleoptericin-A (ColA) is amplified from total *Sitophilus oryzae* cDNA. Expression of ColA in beetles of genus *Sitophilus* regulates titers of γ-Protobacterium, which has naturally developed close symbiotic relationship the beetles, and resides in specific cells called bacteriocytes. (Login, F. H., Balmain, S., Vallier, A., Vincent-Monegat, C., Vigneron, A., Weiss-Gayet, M., Rochat, D., Heddi, A. Antimicrobial peptides keep insect endosymbionts under control. *Science* 334(6054): 362-365 (2011) (which is incorporated by reference in its entirety for all purposes)).

Murine embryonic stem cells comprising gfp+AMB are treated using a neural differentiation protocol. MTB expression levels are quantified using qPCR and fluorescent microscopy. Amplified colA is then expressed in the gfp+AMB embryonic stem cells. A promoter is selected to provide optimal ColA expression levels.

Example 4

Magnetic Pheonotype of Murine Cells Containing gfp+AMB

Cells from macrophage cell line J774.2 derived from murine ascites and solid tumor with introduced gfp+AMB were applied to a magnetic column and were retained by the column. These results demonstrate that, following introduction of gfp$^+$AMB, J774.2 murine cells were magnetically detected and magnetically manipulated, as they were magnetically concentrated and magnetically collected.

Example 5

Gfp$^+$AMB in Human Breast Cancer Cell Line MDA-MB-231

Gfp$^+$AMB, Gfp+InlA/B+AMB, and Gfp+Pla1+AMB were each introduced to human breast cancer cells from cell line MDA-MB-231. GFP fluorescence was detected in more than 90% of the MDA-MB-231 cells 48 hours after the introduction of each of Gfp$^+$AMB, Gfp+InlA/B+AMB, and Gfp+Pla1+AMB. GFP fluorescence in Gfp$^+$AMB was observed in these MDA-MB-231 cells at least 13 days after introduction of gfp$^+$AMB, in the fourth passage of the MDA-MB-231 cells following the introduction, where MDA-MB-231 cell population doubled three to four times between each passage. GFP fluorescence was observed in both forming daughter cells of an MDA-MB-231 cell with introduced gfp$^+$AMB in the process of cell division.

Following the introduction of gfp$^+$AMB, MDA-MB-231 cells were stained with Lysotracker® Red DND-99 dye (specific to lysosomes) and Hoechst 33342 nuclear stain purchased from Life Technologies. Green GFP fluorescence was observed as localized within individual MDA-MB-231 cells and distinct from red lysosome staining and blue nuclear staining suggesting that AMB were localized in cytoplasm and not digested through lysosome pathway.

At 24 hours and 72 hours after introduction, plated MDA-MB-231 cells and plated control MDA-MB-231 cells were fixed in formalin and glutaraldehyde following a wash with PBS. Cells were then stained with Prussian Blue, and observed by microscopy at 40× magnification. Iron staining was observed in some of the MDA-MB-231 cells with introduced gfp$^+$AMB but not in the control MDA-MB-231 cells without introduced gfp$^+$AMB. The proportion of cells displaying iron staining was similar between the MDA-MB-231 cells 72 hours after gfp$^+$AMB introduction and the MDA-MB-231 cells 24 hours after gfp$^+$AMB introduction.

48 hours after the introduction of gfp$^+$AMB, MDA-MB231 cells were trypsinized and resuspended in PBS. One sample of these cells was placed into a glass slide chamber. A magnet was aligned to the side of chamber and cell movement was observed under microscope at 20× magnification. MDA-MB231 cells with introduced gfp$^+$AMB, but not control MDA-MB231 cells which had not had gfp$^+$AMB introduced, exhibited movement toward the magnet. Another sample of these cells was placed into small tubes, which were taped to a magnet for one hour. Control MDA-MB231 cells which had not had gfp$^+$AMB introduced settled down at the bottom of the tube. However, MDA-MB231 cells with introduced gfp$^+$AMB were aligned to the magnet side of the tubes.

These results indicate that gfp$^+$AMB were not immediately cleared from human breast cancer MDA-MB-231 cells. They were transferred to daughter cells across at least 12 cell divisions and were located within the MDA-MB-231 cells outside of both the lysosomes and nuclei. These results also demonstrate that at least 48 hours following introduction of gfp$^+$AMB, the MDA-MB-231 cells containing gfp$^+$AMB displayed were magnetically detected and magnetically manipulated, as they were magnetically moved, magnetically targeted to a location, magnetically concentrated, and magnetically collected. Additionally, at least 72 hours following introduction of gfp$^+$AMB, the MDA-MB-231 cells contained observable quantities of iron.

Example 6

Gfp$^+$AMB in Human Induced Pluripotent Stem Cells

GFP fluorescence was observed in Human Induced Pluripotent Stem ("IPS") cells at least eight days following introduction of gfp$^+$AMB to the IPS cells, in the second passage of the IPS cells. These results indicate that gfp$^+$AMB were not immediately cleared from human IPS cells, and were transferred to daughter cells.

Example 7

Cell Imaging within Mouse Tumor

Cell visualization was tested in a mouse bearing two subcutaneous tumors, one on its left flank and one on its right flank. $1.5 \times 10^6$ MDA-MB231 cells containing introduced gfp$^+$AMB were injected directly into the tumor on the left flank of the mouse. An equivalent number of control MDA-MB231 cells without introduced cells were injected on the right flank of the mouse. The mouse was imaged using a bench top IT MRI with T2w pulse sequences. The resulting image showed a dark area at the tumor on the left side of the mouse, the site of the injection of MDA-MB231 cells containing introduced gfp$^+$AMB, but no signal at the tumor on the right side of the mouse, where control MDA-MB231 cells injected into a left side tumor.

Example 8

Monitoring of Mouse Tumor

Gfp$^+$AMB cells are introduced into MDA-MB231 human cancer cells. The resulting magnetic cells and their daughter cells are injected into mammary fat pads of a group of immunocompromized mice. Tumor growth is monitored at regular intervals by MRI imaging. Mice with established tumors assigned either to an experimental group or to a control group. Mice in the experimental group are treated with a potential anti-tumor therapeutic compound while mice in the control group are treated with an inactive vehicle. MRI is used to monitor the size and growth of the tumor non-invasively following the treatments to assess the efficacy of the tested compound in combatting the tumor.

Example 9

Magnetic Enhancement of Cell Retention

Gfp$^+$AMB cells are introduced into Rat Cardiac-Derived Stem Cells (CDC). The resulting magnetic CDC cells are used in the Ischemia/Reperfusion model. Rats are treated as described Cheng K, Malliaras K, Li T S, Sun B, Houde C, Galang G, Smith J, Matsushita N, Marban E. Magnetic enhancement of cell retention, engraftment, and functional benefit after intracoronary delivery of cardiac-derived stem cells in a rat model of ischemia/reperfusion. Cell Transplant. 2012; 21(6):1121-35. The magnetic CDC cells are then introduced into the left ventricle cavity of the treated rates. A 1.3 T magnet is placed above the heart during and after the injection. The animal's chest is closed and it is allowed to recover.

The short and long-term behavior of the labeled CDC in the rat is monitored by MRI imaging at regular intervals.

Example 10

AMF tumor treatment

Gfp+AMB cells are introduced into MDA-MB231 cells. The resulting cells are injected into subcutaneous tumors, formed by 4T1 cells in nude mice. Untreated control MDA-MB231 cells are injected into a tumor at the opposite flank of each animal. Each animal is placed into alternating magnetic field (30.6 kA/m, 118 kHz) for 30 minutes, and allowed to recover following the procedure. Animals are sacrificed at regular intervals and histological analyzes are performed on tumors from both mice with injected magnetic MDA-MB231 and control mice with injected control MDA-MB231. In the experimental mice, the labeled cells and the surrounding tumor are damaged leading to damage to the tumor overtime.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method of detecting a eukaryotic cell, comprising magnetically imaging a eukaryotic cell containing at least one magnetotactic bacterium, wherein the eukaryotic cell is capable of undergoing at least three cell divisions and wherein the magnetotactic bacterium is capable of being transferred to daughter cells of the eukaryotic cell through at least three cell divisions.

2. The method according to claim 1, wherein the eukaryotic cell is contained within an animal.

3. The method according to claim 2, wherein the animal is a mammal.

4. The method according to claim 3, wherein the mammal is murine.

5. The method according to claim 3, wherein the mammal is human.

6. The method according to claim 3, wherein the eukaryotic cell is a cancer cell.

7. The method according to claim 6, wherein the mammal has been treated with a potential anti-tumor agent.

8. The method according to claim 3, wherein the eukaryotic cell is or was derived from an IPS cell.

9. A method of magnetically manipulating a eukaryotic cell, comprising magnetically localizing a eukaryotic cell containing at least one magnetotactic bacteria, wherein the eukaryotic cell is capable of undergoing at least three cell divisions and wherein the magnetotactic bacterium is capable of being transferred to daughter cells of the eukaryotic cell through at least three cell divisions.

10. The method according to claim 9, wherein the eukaryotic cell is contained in an animal.

11. The method according to claim 10, wherein the animal is a mammal.

12. The method according to claim 11, wherein the animal is murine.

13. The method according to claim 11, wherein the animal is human.

14. The method according to claim 11, wherein the eukaryotic cell is localized to a tumor.

15. A method of damaging a eukaryotic cell, comprising subjecting a eukaryotic cell to an alternating magnetic field or a spinning magnetic field, wherein the eukaryotic cell contains at least one magnetotactic bacterium, wherein the eukaryotic cell is capable of undergoing at least three cell divisions and wherein the magnetotactic bacterium is capable of being transferred to daughter cells of the eukaryotic cell through at least three cell divisions.

16. The method according to claim 15, wherein the eukaryotic cell is contained in an animal.

17. The method according to claim 16, wherein the animal is a mammal.

18. The method according to claim 17, wherein the mammal is murine.

19. The method according to claim 17, wherein the mammal is human.

20. The method according to claim 17, wherein the eukaryotic cell is a cancer cell or has been targeted to a tumor.

21. The method according to claim 2, wherein the eukaryotic cell has been introduced into an animal.

22. The method according to claim 21, wherein the animal is a mammal.

23. The method according to claim 22, wherein the mammal is murine.

24. The method according to claim 22, wherein the mammal is human.

25. The method according to claim 10, wherein the eukaryotic cell has been introduced into an animal.

26. The method according to claim 25, wherein the animal is a mammal.

27. The method according to claim 26, wherein the animal is murine.

28. The method according to claim 26, wherein the animal is human.

29. The method according to claim 16, wherein the eukaryotic cell has been introduced into an animal.

30. The method according to claim 29, wherein the animal is a mammal.

31. The method according to claim 30, wherein the mammal is murine.

32. The method according to claim 30, wherein the mammal is human.

* * * * *